(12) United States Patent
Lee et al.

(10) Patent No.: US 8,062,628 B2
(45) Date of Patent: Nov. 22, 2011

(54) DEODORANT PATCH AND METHOD FOR MAKING

(76) Inventors: Gregory Lee, Calumet City, IL (US); Tawana G. Lee, Calumet City, IL (US)

( * ) Notice: Subject to any disclaimer, the term of this patent is extended or adjusted under 35 U.S.C. 154(b) by 371 days.

(21) Appl. No.: 11/724,095

(22) Filed: Mar. 14, 2007

(65) Prior Publication Data

US 2007/0218092 A1    Sep. 20, 2007

Related U.S. Application Data

(60) Provisional application No. 60/767,322, filed on Mar. 17, 2006.

(51) Int. Cl.
    *A61K 8/00*      (2006.01)
    *A61K 8/02*      (2006.01)

(52) U.S. Cl. .......................... 424/65; 424/401

(58) Field of Classification Search .......... None
See application file for complete search history.

(56) References Cited

U.S. PATENT DOCUMENTS

| | | | |
|---|---|---|---|
| 2,669,720 A | 2/1954 | Vandekerck | |
| 3,156,924 A | 11/1964 | Wonacott | |
| 4,485,492 A | 12/1984 | Sneider | |
| 4,631,752 A | 12/1986 | Heyman et al. | |
| 4,747,162 A | 5/1988 | Yanagihara | |
| 5,403,588 A | 4/1995 | Santa Ana, Jr. | |
| 5,732,485 A * | 3/1998 | Laughlin et al. | 36/136 |
| 5,780,047 A * | 7/1998 | Kamiya et al. | 424/443 |
| 6,162,457 A * | 12/2000 | Martz | 424/448 |
| 6,770,286 B1 * | 8/2004 | Berry | 424/402 |
| 7,241,411 B2 * | 7/2007 | Berry et al. | 264/160 |
| 2005/0070857 A1 * | 3/2005 | Courns | 604/312 |
| 2006/0041987 A1 * | 3/2006 | Villain | 2/53 |

FOREIGN PATENT DOCUMENTS

WO    WO 2004024113 A1 *   3/2004

OTHER PUBLICATIONS

Published by Unilever, http://www.antiperspirantsinfo.com/english/ingredients.php "What's in an Antiperspirant?" (2 pages).

* cited by examiner

*Primary Examiner* — Sreeni Padmanabhan
*Assistant Examiner* — Layla Soroush
(74) *Attorney, Agent, or Firm* — Pauley Petersen & Erickson

(57) ABSTRACT

This invention relates generally to an underarm hygiene product having the form of a deodorant patch between a top carrier sheet and a bottom carrier sheet. Deodorant patches dissolve upon contact with the underarm skin and provide a discreet, portable method of remaining fresh in any time or place. Convenient one time dispensing by a flat patch eliminates the need for bulky containers and provides an elegant solution to limitations on quantities of personal care products during airline flights while away from home. This invention also relates to a method of producing the underarm hygiene product.

18 Claims, 3 Drawing Sheets

DEODORANT PATCH AND METHOD FOR MAKING

CROSS REFERENCE TO RELATED APPLICATION

This application claims the benefit of U.S. Provisional Application No. 60/767,322 filed on 17 Mar. 2006.

BACKGROUND OF THE INVENTION

1. Field of the Invention

This invention relates generally to an underarm hygiene product having the form of a deodorant patch between a top carrier sheet and a bottom carrier sheet.

2. Discussion of Related Art

It is known to use disposable, non-disposable (launderable) and partially disposable garment shields for protecting clothing from perspiration by attaching them directly to apparel such as a dress. Some conventional garment shields have absorption properties to capture perspiration and others offer barrier properties to keep perspiration from contacting the garment. It is also known to modify conventional garment shields with an adhesive for attachment directly to the skin of a wearer.

Deodorants and antiperspirants are also known for underarm hygiene purposes. These compounds have a limited number of dispensing options for application by the user. Common deodorant application forms are roll-on, aerosol, stick, gel and cream. All of these dispensing containers (even "travel size") provide sufficient quantities for multiple uses of deodorant material to last several days or weeks.

SUMMARY OF THE INVENTION

It is desirable to provide a portable, economical, single-use dispenser of deodorant. From the above, there is a need for an improved method of dispensing deodorant and to provide improved hygiene and personal freshness in a convenient take-anywhere form.

The above and other objects of this invention can be attained, at least in part, with an underarm hygiene product including a deodorant patch with a first side and an opposite side while having a thickness and size suitable for placement under the arm. The patch may be constructed where the deodorant dissolves following skin contact with a user. The underarm hygiene product may further include a top carrier sheet positioned on the first side of the deodorant patch and a bottom carrier sheet positioned on the opposite side of the deodorant patch.

The deodorant may dissolve in under or less than ten minutes or desirably 3 to 5 seconds at a temperature between about 33.3 degrees C. and about 37.8 degrees C. The deodorant patch may have one of a circular shape, a rectangular shape and an annular shape wherein the deodorant patch has an area of about 4 square centimeters to about 150 square centimeters and an outer width of about 3 centimeters to about 10 centimeters. The deodorant patch may have a thickness of about 15 micrometers to about 150 micrometers and maybe flexible. At least one of the first side of the deodorant patch and the opposite side of the deodorant patch may include an adhesive.

The deodorant may perform at least one of the functions of preventing, masking and destroying odors and may include antiperspirant capabilities. The deodorant may include a fragrance and in particular such fragrance may be selected from the group consisting of regular scented, unscented or powder fresh.

According to a preferred embodiment of this invention, the deodorant patch includes aluminum zirconium tetrachlorohydrex GLY, cyclomethicone, stearyl alcohol, octyl isononanoate, talc, hydrogenated vegetable oil, glyceryl stearate, fragrance, BHT, T-butyl hydroquinone, starch, polyol, and PEG-100 stearate.

At least one of the top carrier sheet and the bottom carrier sheet may be made from one of the group consisting of paper, plastic, foil or combinations thereof and may include a release agent or an adhesive. The top carrier sheet and the bottom carrier sheet may bond together to form a seal around the deodorant patch.

The invention further includes a method of producing an underarm hygiene product that may include: melting a deodorant material; spreading or molding the deodorant material into a form; cooling the form; shaping or slicing the form into a deodorant patch; laminating the deodorant patch between a top carrier sheet and a bottom carrier sheet.

Other objects and advantages will be apparent to those skilled in the art from the following detailed description taken in conjunction with the appended claims and the drawings.

BRIEF DESCRIPTION OF THE DRAWINGS

The above and other objects of this invention can be better understood when the specification is read in view of the drawings, wherein.

DETAILED DESCRIPTION OF THE INVENTION

Figure 1:
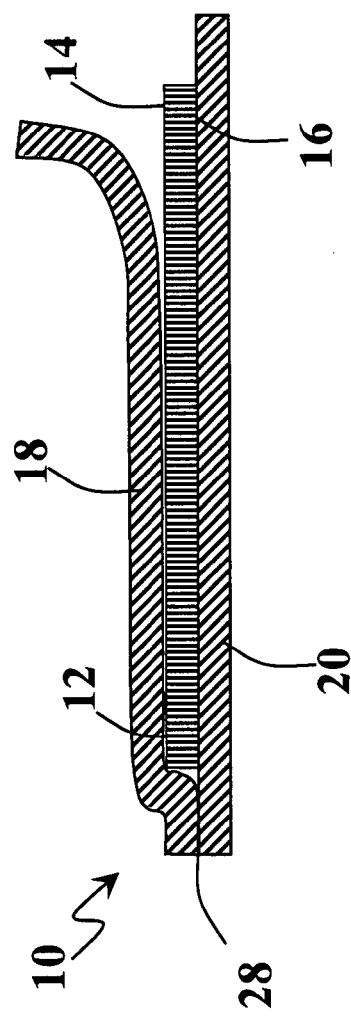
FIG. 1 is a sectional view of an underarm hygiene product, according to one preferred embodiment of this invention.

FIG. 1 shows a cross sectional view of underarm hygiene product 10, according to a preferred embodiment of this invention. Underarm hygiene product 10 may include deodorant patch 12, top carrier sheet 18 and bottom carrier sheet 20.

Deodorant patch 12 or w may have first side 14 and opposite side 16. Deodorant patch 12 may be generally adapted for underarm use. Deodorant patch 12 may be relatively thin, such as, for example, about 15 micrometers to about 150 micrometers, desirably about 30 micrometers to about 75 micrometers. According to a preferred embodiment of this invention, deodorant patch 12 has a thickness of about 50 micrometers.

A suitable size for deodorant patch 12 may include an outer width of about 3 centimeters to about 10 centimeters and desirably about 4 centimeters to about 7 centimeters. In practice, small, medium, large and extra large sizes of deodorant patch 12 may be produced. According to a preferred embodiment of this invention, deodorant patch 12 has an outer width of about 5 centimeters.

Suitable areas for deodorant patch 12 may include about 4 square centimeters to about 150 square centimeters and desirably about 10 square centimeters to about 100 square centimeters. According to a preferred embodiment of this invention, deodorant patch 12 has an area of about 80 square centimeters.

Figure 2C:
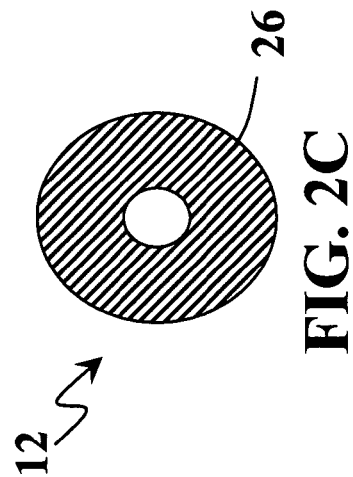
FIG. 2C is a sectional view of a deodorant patch, according to a preferred embodiment of this invention.
Figure 2B:
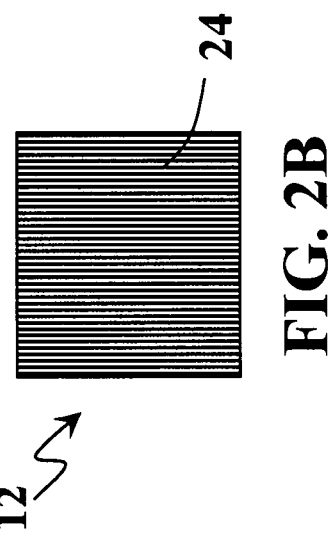
FIG. 2B is a sectional view of a deodorant patch, according to a preferred embodiment of this invention.
Figure 2A:
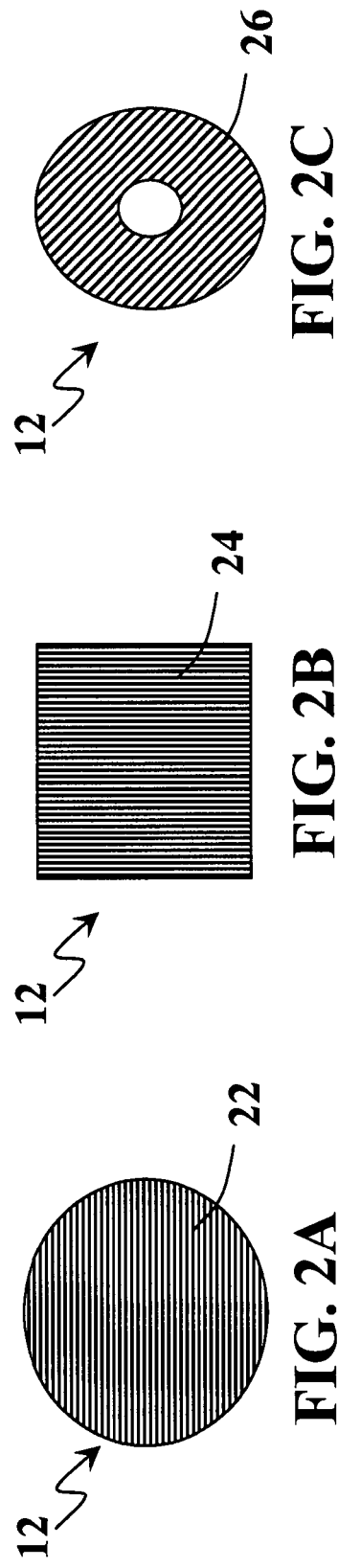
FIG. 2A is a sectional view of a deodorant patch, according to a preferred embodiment of this invention.

As shown in FIG. 2A-2C, suitable shapes for deodorant patch 12 may include circular shape 22, rectangular shape 24, annular shape 26 (ring) or any other suitable geometric, linear or arcuate form. According to a preferred embodiment of this invention, deodorant patch 12 has a generally elliptical shape.

Generally, deodorant patch 12 dissolves following contact with the skin of user 30. Desirable deodorant formulations allow for handling, positioning or repositioning of deodorant patch 12 during application so as not to significantly dissolve in a hand of user 30. Typically, dissolving occurs due to the elevated temperature of skin and in particular the warmth above the ambient surroundings in an underarm of user 30. Dissolving may include melting at least a part of the deodorant material. Suitable deodorant melting temperatures may range from about 33.3 degrees C. to about 37.8 degrees C., and desirably from about 34.5 degrees C. to about 36 degrees C. According to a preferred embodiment of this invention, deodorant patch 12 dissolves at about 35.5 degrees C.

Typically, deodorant patch 12 may dissolve, melt, soften or be absorbed after less than about 10 minutes in contact with skin. Desirably, deodorant patch 12 may dissolve in about 2 minutes to about 4 minutes following placement and lowering of an arm of user 30. Deodorant patch 12 may include formulations to allow spreading or increasing area while dissolving or may include formulations to resist spreading. According to a preferred embodiment of this invention, deodorant patch 12 dissolves in about 3 seconds to about 5 seconds.

Deodorant patch 12 may perform more than one hygiene function. Desirably, deodorant patch 12 may prevent, mask and/or destroy odors. Odors often come from a combination of skin secretions and bacteria which consume the skin secretions before emitting pungent or undesirably aromatic odors. One method to control odors is to reduce the presence of bacteria such as by antimicrobial or antibacterial agents. Another method to control odors as well as unsightly wetting of clothing at the armpits may include using an antiperspirant agent such as a salt to reduce the amount of sweat on the skin. According to a preferred embodiment of this invention, the antiperspirant agent is aluminum zirconium tetrachlorohydrex GLY.

Suitable deodorant formulations may include, for example, fragrances, skin conditioners, skin softeners, emollients, moisturizers, masking oils (to minimize drying out and showing a residue), cooling agents, oil absorbing agents, wash off agents, antioxidants, colorings, pigments, carrier agents, fillers, propellants and any other suitable agent/material to improve consumer enjoyment and/or effectiveness. According to a preferred embodiment of this invention, the deodorant formulation includes aluminum zirconium tetrachlorohydrex GLY, cyclomethicone, stearyl alcohol, octyl isonanoate, talc, hydrogenated vegetable oil, glyceryl stearate, fragrance, BHT, T-butyl hydroquinone, starch, polyol, and PEG-100 stearate.

Another desirable attribute of deodorant patch 12 may include some degree of flexibility or resilience. This may allow for better handling characteristics of deodorant patch 12 so that during transportation, such as, for example in a fully loaded suitcase, deodorant patch 12 does not become broken into pieces upon jostling of the suitcase as may happen during luggage loading on an airplane. Flexibility, may be increased by deodorant formulations including polymer and/or plastic like materials such as waxes and the like.

Deodorant patch 12 may include any desirable fragrance. Often fragrances can be gender specific and tailored to consumer preferences. Deodorant patch 12 may include any known fragrances, especially those complimenting or matching existing brands of perfumes, aftershaves, deodorants, antiperspirants and/or colognes. This may allow user 30 to enjoy the same fragrance during travel as when at home. According to a preferred embodiment of this invention, the fragrance is selected from the group consisting of regular scented, unscented or powder fresh.

Deodorant patch 12 may include an adhesive material applied to at least first side 14 and/or opposite side 16. Suitable adhesives may either dissolve with deodorant patch 12 when applied to the underarm or remain for removal, such as, for example, during a shower. Desirably, substantially all of or the entire deodorant patch 12 dissolves completely with minimal residue and no more than conventional deodorant products. Other possible embodiments of deodorant patch 12 may include nondissolving or less dissolving materials, and such materials may include absorbents such as natural or synthetic gauze or terry cloths to capture perspiration. Other less dissolving material may include reinforcement to provide structural stability and/or support, such as, for example from loose bulk fibers. Additionally, barrier materials such as cellulose or plastic films may be included to prevent perspiration from contacting outer garments.

Underarm hygiene product 10 may include top carrier sheet 18 positioned on first side 14 of deodorant patch 12 and bottom carrier sheet 20 positioned on opposite side 16 of deodorant patch 12. Positioned may include touching, contacting, adhering and any other suitable mounting configuration to facilitate packaging and application of deodorant patch 12. Generally, top carrier sheet 18 and/or bottom carrier sheet 20 may include a substantially thin material to aid in portability and provide protection for deodorant patch 12. Desirably, these sheets are a low-cost material such as paper, plastic, foil, combinations thereof or any other suitable material to contain, isolate, sandwich, laminate and convey deodorant patch 12. According to a preferred embodiment, carrier sheets 18, 20 are made from 20 pound paper. Alternatively, at least one of carrier sheets 18, 20 may be or may include a relatively stiff material to prevent deodorant patch 12 from flexing before application.

At least a portion of one of carrier sheets 18, 20 may include a release agent to facilitate application of deodorant patch 12. Suitable release agents are compatible with the deodorant formulation and substantially little or none of deodorant patch 12 becomes affixed to carrier sheets 18, 20 when treated with a release agent during production, distribution and storage prior to use. Material similar to a typical label backing sheet may form suitable carrier sheets 18, 20. According to a preferred embodiment of this invention, top carrier sheet 18 is printable paper treated with a wax.

At least a portion of one of carrier sheets 18, 20 may include an adhesive to facilitate application of deodorant patch 12. Suitable adhesives are compatible with the deodorant formulation and substantially the entire or all of deodorant patch 12 remains affixed to carrier sheets 18, 20 when treated with adhesive during production, distribution and storage prior to use. Pressure sensitive paper such as commonly used for labels may form suitable carrier sheets 18, 20. According to a preferred embodiment of this invention, bottom carrier sheet 20 is treated with a water soluble glue.

Top carrier sheet 18 and bottom carrier sheet 20 may extend beyond a perimeter of deodorant patch 12. Desirably, top carrier sheet 18 and bottom carrier sheet 20 include a lip or an edge suitable for sealing, such as, for example by adhesive or crimping to form a seal around deodorant patch 12. An opening aid such as a notch, perforation, string or any other suitable mechanism to facilitate application may be included.

Figure 5:
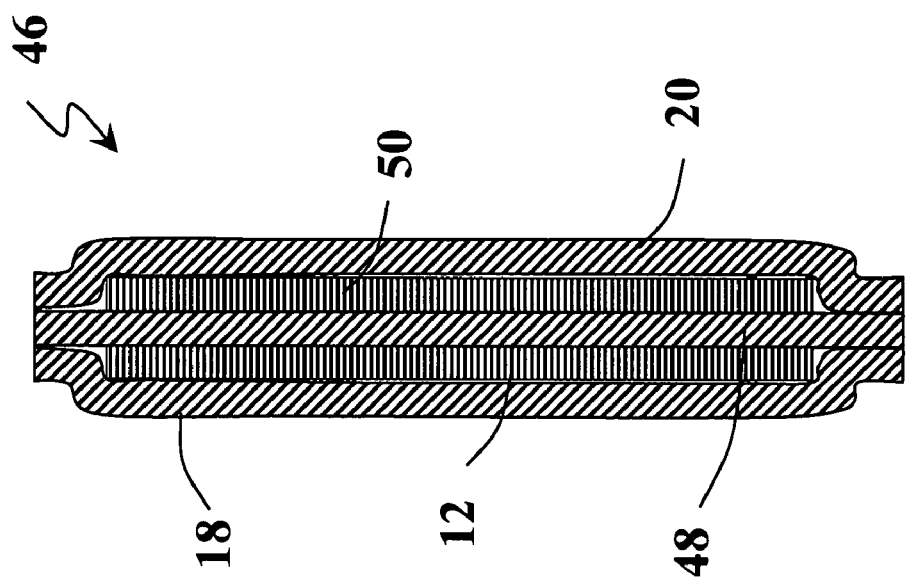
FIG. 5 is a sectional view of a dual dispensing configuration, according to one preferred embodiment of this invention.

One or more deodorant patches 12 may be sealed within carrier sheets 18, 20. A package of two deodorant patches 12 may ensure user 30 of having one for each side. As shown in FIG. 5 and according to a preferred embodiment of this invention, dual dispensing configuration 46 may include top carrier sheet 18 adjacent to, disposed on or positioned next to deodorant patch 12 with optional divider sheet 48 adjacent to second deodorant patch 50 which is adjacent to bottom carrier sheet 20. Divider sheet 48 may include adhesive and/or release agents.

Keeping deodorant fresh and fragrance contained before use may improve shelf life of underarm hygiene product 10. According to a preferred embodiment of this invention, a substantially air tight enclosure or seal 28, as shown in FIG. 1, is formed by top carrier sheet 18 and bottom carrier sheet 20 around deodorant patch 12.

Figure 3:
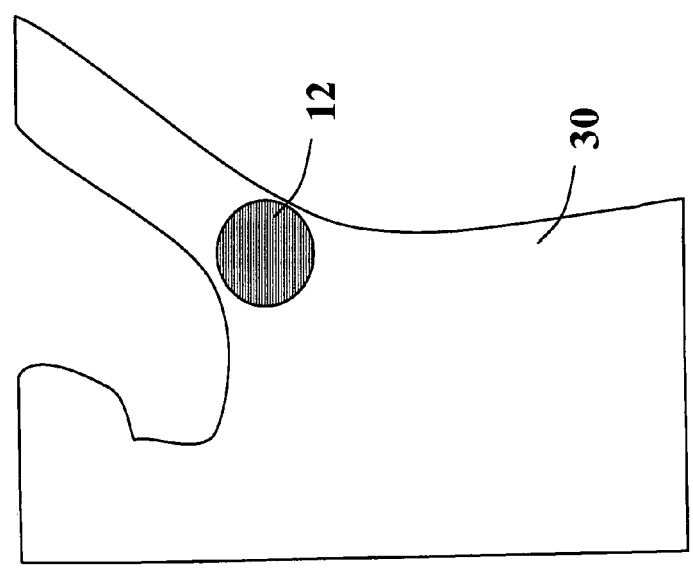
FIG. 3 is a partial sectional view of a user of an underarm hygiene product, according to one preferred embodiment of this invention.

As shown in FIG. 3, user 30 may apply deodorant patch 12 to underarm area or armpit. Desirably, user 30 removes one of carrier sheets 18, 20 from underarm hygiene product 10 and places or locates deodorant patch 12 and remaining carrier sheet 18, 20 to the underarm area with the deodorant patch 12 contacting underarm skin. User 30 may then remove remaining carrier sheet 18, 20 and lower arm desirably until deodorant patch 12 is at least partially dissolved and repeat for the other side. User 30 may perform this procedure as desired to maintain freshness.

User 30 may remove deodorant patch 12 and discard prior to next cleaning such as in a shower, especially if there are nondissolving components. Desirably, underarm hygiene product 10 and the components therein are at least substantially or fully biodegradable and/or hypoallergenic. According to a preferred embodiment of this invention, user 30 has nothing to remove following use.

As described above individual underarm hygiene product 10 includes "peel 'n stick" features which may be particularly useful when traveling to avoid carrying a bulky convention deodorant container. Additional uses may include one time application, such as, for example, in hospitals, nursing homes, hotels, motels, and/or as promotional items. Typical retail packaging (box) may include quantities of 6, 12, 24 or any other convenient amount. Alternate embodiments may include a single larger resealable container with deodorant patch 12 lacking carrier sheets 18, 20 and only a separation layer between deodorant patches or wafers of deodorant.

Figure 4:
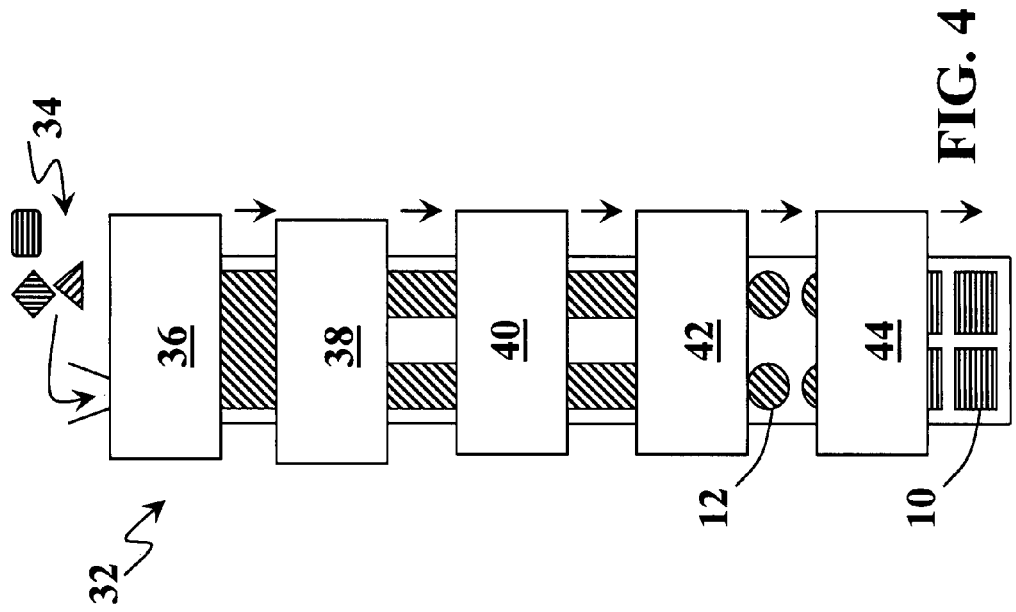
FIG. 4 is a schematic of a manufacturing process, according to one preferred embodiment of this invention.

As schematically shown in FIG. 4, a method for producing underarm hygiene product 10 may include a manufacturing process 32. Manufacturing process 32 may include the steps of combining or mixing ingredients 34 and melting 36 them. Additional steps may include spreading 38 or molding the deodorant material into a form and cooling 40 of the form. According to a preferred embodiment of this invention a design or insignia is applied, inlaid or embossed during the forming step.

Depending on the methods used to make the form, a shaping step 42 may be needed to trim excess material or thinly slice deodorant patches 12. The method may also include the application of carrier sheets 18, 20 in a lamination step 44 which may include sealing the carrier sheets 18, 20 together. One skilled in the art and guided by the teachings herein will readily appreciate that one or more of the above steps may be omitted or performed in an order other than stated without departing from the spirit of this invention. Other manufacturing steps such as printing, boxing, palletizing and any other suitable steps may be included in the method.

While in the foregoing specification this invention has been described in relation to certain embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. An underarm hygiene product comprising:
   a deodorant patch consisting of a single deodorant formulation formed in a single layer with a first side and an opposite side having a thickness and size suitable for placement under an arm, wherein the deodorant formulation melts or softens following skin contact with minimal residue for a user; and
   a top carrier sheet positioned on the first side of the deodorant patch and a bottom carrier sheet positioned on the opposite side of the deodorant patch, wherein at least one of the top carrier sheet and the bottom carrier sheet includes a release agent to facilitate application and release of the deodorant patch from the top carrier sheet and onto the underarm.

2. The underarm hygiene product of claim 1, wherein the single deodorant formulation melts or softens in under ten minutes.

3. The underarm hygiene product of claim 1, wherein the deodorant patch has one of a circular shape, a rectangular shape and an annular shape.

4. The underarm hygiene product of claim 3, wherein the deodorant patch has an area of about 4 square centimeters to about 150 square centimeters.

5. The underarm hygiene product of claim 3, wherein the deodorant patch has an outer width of about 3 centimeters to about 10 centimeters.

6. The underarm hygiene product of claim 1, wherein the deodorant patch has a thickness of about 15 micrometers to about 150 micrometers.

7. The underarm hygiene product of claim 1, further comprising an adhesive applied to at least one of the first side of the deodorant patch and the opposite side of the deodorant patch.

8. The underarm hygiene product of claim 1, wherein at least one of the top carrier sheet and the bottom carrier sheet includes an adhesive.

9. The underarm hygiene product of claim 1, wherein the top carrier sheet and the bottom carrier sheet bond together to form a seal around the deodorant patch.

10. The underarm hygiene product of claim 1, wherein the single deodorant formulation includes aluminum zirconium tetrachlorohydrex GLY, cyclomethicone, stearyl alcohol, octyl isonanoate, talc, hydrogenated vegetable oil, glyceryl stearate, fragrance, BHT, T-butyl hydroquinone, starch, polyol, and PEG-100 stearate.

11. The underarm hygiene product of claim 1, wherein the top carrier sheet and the bottom carrier sheet are made from one of the group consisting of paper, plastic, foil and combinations thereof.

12. The underarm hygiene product of claim 1, wherein the deodorant patch is flexible.

13. An underarm hygiene product consisting of:
   a first deodorant patch consisting of a single deodorant formulation formed in a single layer with a first side and an opposite side having a thickness and size suitable for placement under an arm, wherein the single deodorant formulation melts or softens following skin contact with minimal residue for a user;

a second deodorant patch consisting of the single deodorant formulation formed in a single layer with a first side and an opposite side having a thickness and size suitable for placement under an arm, wherein the single deodorant formulation melts or softens following skin contact with minimal residue for a user;

a divider sheet positioned between the first deodorant patch and the second deodorant patch; and a top carrier sheet positioned on the first side of the first deodorant patch and a bottom carrier sheet positioned on the opposite side of the second deodorant patch, wherein at least one of the top carrier sheet, the bottom carrier sheet, and the divider sheet includes a release agent to facilitate application and release of the deodorant patch onto the underarm.

14. An underarm hygiene product comprising:

a deodorant patch consisting of a single deodorant formulation formed in a single layer;

the single deodorant formulation comprising aluminum zirconium tetrachlorohydrex GLY, cyclomethicone, stearyl alcohol, octyl isonanoate, talc, hydrogenated vegetable oil, glyceryl stearate, fragrance, BHT, T-butyl hydroquinone, starch, polyol, and PEG-100 stearate, wherein the deodorant formulation that melts or softens in about 3 seconds to about 5 seconds at temperature between about 33.3 degrees C. and about 37.8 degrees C. with minimal residue; and a top carrier sheet and a bottom carrier sheet sandwiching the deodorant patch of deodorant therein, wherein at least one of the top carrier sheet and the bottom carrier sheet includes a release agent to facilitate application and release of the deodorant patch from at least one of the top carrier sheet and the bottom carrier sheet onto the underarm.

15. The underarm hygiene product of claim 14, wherein the deodorant performs at least one of the functions of preventing, masking and destroying odors.

16. The underarm hygiene product of claim 14 wherein the deodorant includes antiperspirant capabilities.

17. A method of producing the deodorant patch of claim 1 comprising:

melting a deodorant material consisting of the single deodorant formulation;

spreading or molding the deodorant material into a form;

cooling the form;

shaping the form into the deodorant patch.

18. The method of producing an underarm hygiene product of claim 17, wherein the shaping step includes slicing individual thin patches from the form.

* * * * *